United States Patent [19]
Schatz

[11] Patent Number: 5,108,366
[45] Date of Patent: Apr. 28, 1992

[54] DELIVERY CATHETER

[75] Inventor: Richard A. Schatz, San Diego, Calif.

[73] Assignee: OvaMed Corporation, Palo Alto, Calif.

[21] Appl. No.: 589,794

[22] Filed: Sep. 28, 1990

[51] Int. Cl.5 .................................................. A61M 37/02
[52] U.S. Cl. ............................................ 604/55; 604/28; 604/280
[58] Field of Search ................... 604/27, 28, 164, 280, 604/173, 19, 55

[56] References Cited

U.S. PATENT DOCUMENTS

| | | | |
|---|---|---|---|
| 1,060,665 | 5/1913 | Bell . | |
| 2,574,840 | 11/1951 | Pieri et al. | 128/349 |
| 2,688,329 | 9/1954 | Wallace | 128/349 |
| 3,421,509 | 1/1969 | Fiore | 604/280 |
| 3,467,101 | 9/1969 | Fogarty et al. | 128/348 |
| 3,593,713 | 7/1971 | Bogoff | 604/27 |
| 3,605,725 | 9/1971 | Bentov | 128/2.05 R |
| 3,982,546 | 9/1976 | Friend | 605/173 |
| 3,983,864 | 10/1976 | Sielaff et al. | 604/27 |
| 4,033,331 | 7/1977 | Guss et al. | 128/2 M |
| 4,126,134 | 11/1978 | Bolduc et al. | 604/55 |
| 4,195,637 | 4/1980 | Grüntzig et al. | 128/348 |
| 4,307,722 | 12/1981 | Evans | 128/344 |
| 4,323,071 | 4/1982 | Simpson et al. | 128/343 |
| 4,324,262 | 4/1982 | Hall | 604/28 |
| 4,325,337 | 4/1982 | Helfer | 604/28 |
| 4,345,606 | 3/1982 | Littleford | 604/28 |
| 4,502,482 | 3/1985 | DeLuccia et al. | 128/207.15 |
| 4,545,390 | 10/1985 | Leary | 128/772 |
| 4,585,438 | 4/1986 | Makler | 604/55 |
| 4,586,923 | 5/1986 | Gould et al. | 604/95 |
| 4,619,643 | 10/1986 | Bal | 604/43 |
| 4,650,467 | 3/1987 | Bonello et al. | 604/95 |
| 4,652,255 | 3/1987 | Martinez | 604/27 |
| 4,654,025 | 3/1987 | Cassou et al. | 604/55 |
| 4,655,214 | 4/1987 | Linder | 128/207.18 |
| 4,790,814 | 12/1988 | Fischl et al. | 604/55 |
| 4,825,865 | 5/1989 | Zelman | 604/27 |
| 4,881,542 | 11/1989 | Schmidt et al. | 604/27 |
| 5,021,044 | 6/1991 | Sharkawy | 604/164 |

FOREIGN PATENT DOCUMENTS 2125296  3/1984  United Kingdom .................. 604/27

Primary Examiner—Paul J. Hirsch
Attorney, Agent, or Firm—Nydegger & Associates

[57] ABSTRACT

A delivery catheter for introducing living matter into a body passageway or cavity of a female mammal comprises a hollow, flexible, substantially tubular-shaped collection chamber for holding the living matter. An ejection port is formed adjacent to the distal end of the collection chamber and an actuator port is formed at its proximal end. A guide tube having a lumen, is positioned coaxially within the collection chamber with the respective distal and proximal ends of the guide tube and the collection chamber joined together in fluid-tight sealing engagements. In operation, the delivery catheter is inserted into the body passageway over a prepositioned guide wire. More specifically, the delivery catheter receives the guide wire through the lumen of its guide tube to advance the delivery catheter along the guide wire. Once the ejection port of the collection chamber is positioned at the desired site in the body passageway, fluid is introduced into the collection chamber through the actuator port to eject the living matter through the ejection port and into the body passageway. The delivery catheter and the guide wire are then withdrawn from the passageway.

16 Claims, 3 Drawing Sheets

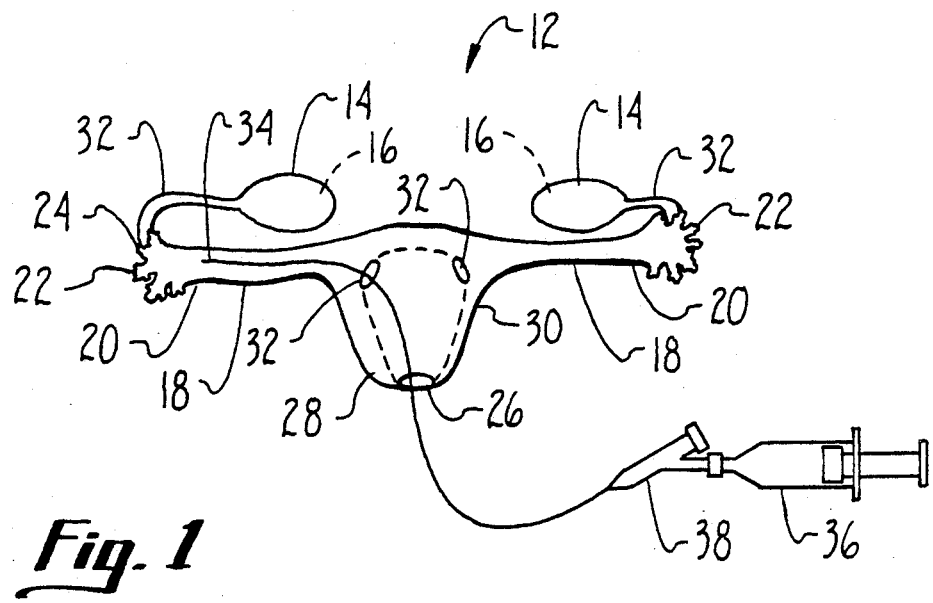
Fig. 1
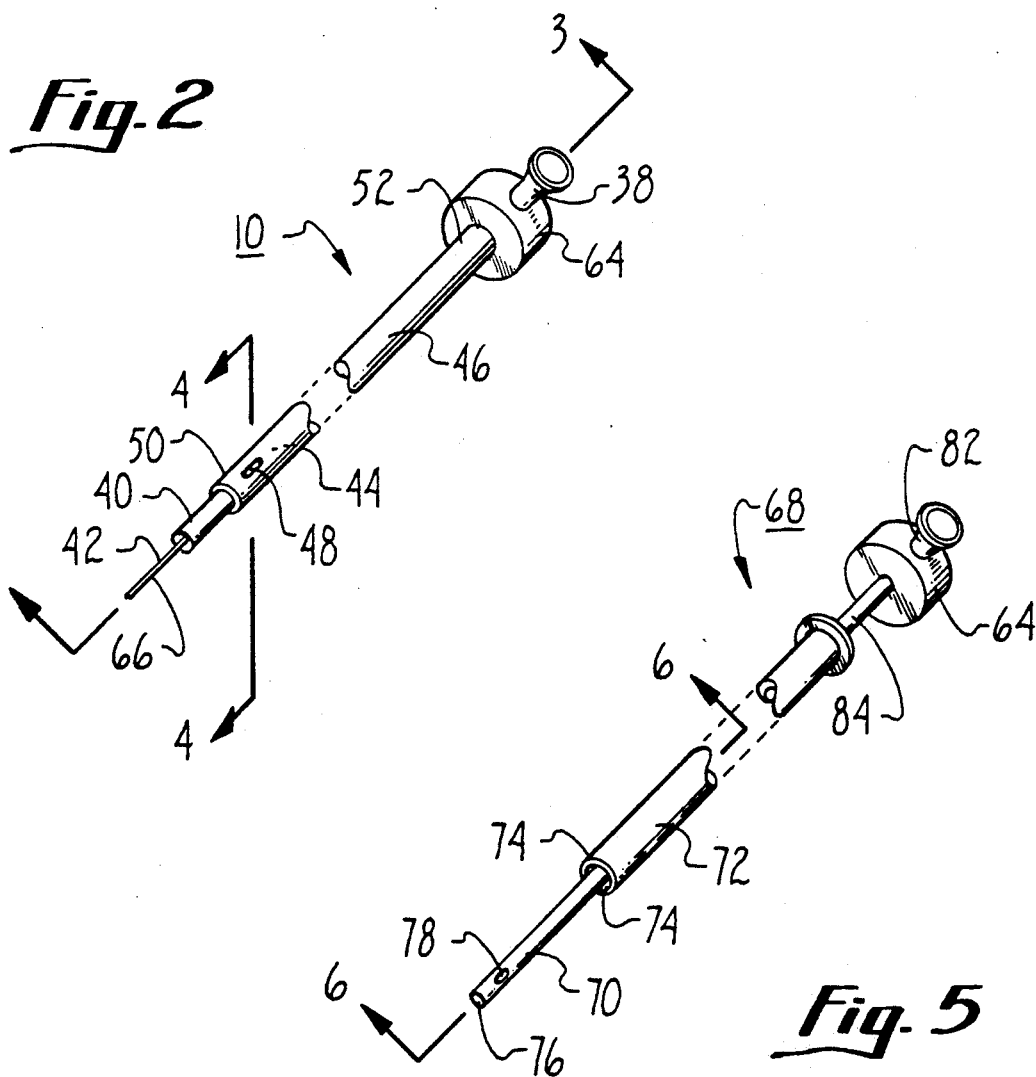
Fig. 2
Fig. 5

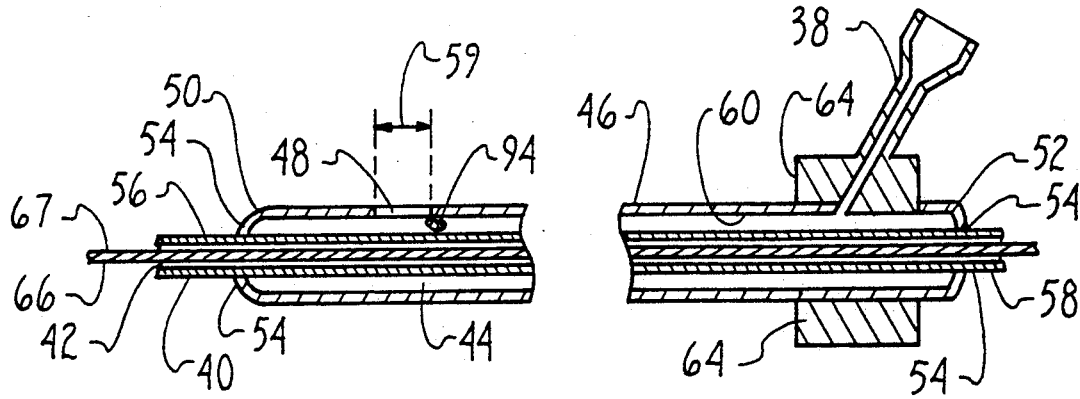
*Fig. 3*
*Fig. 4*
*Fig. 6*
*Fig. 7*
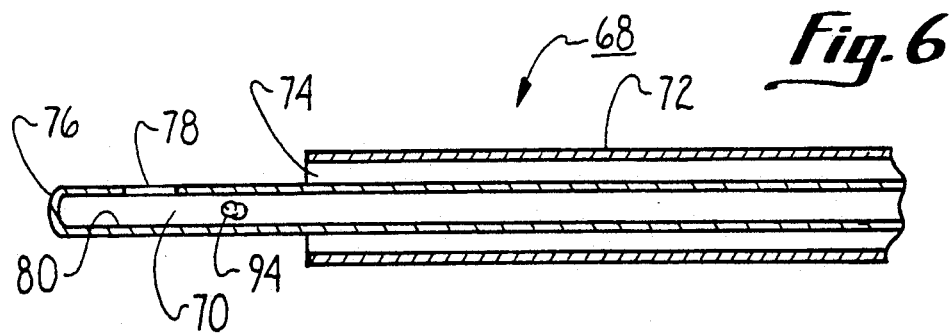
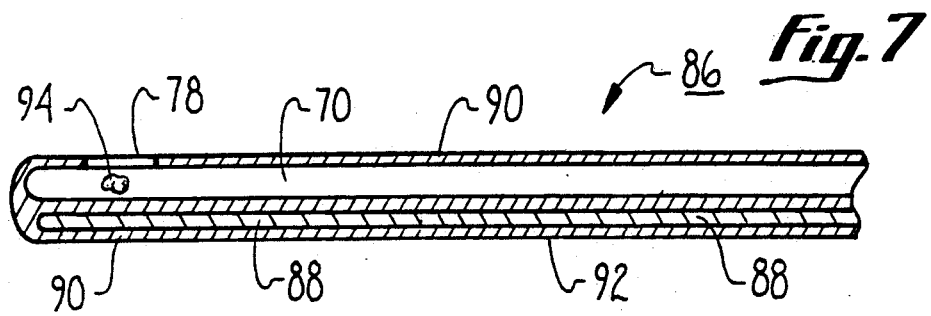

DELIVERY CATHETER

FIELD OF THE INVENTION

The present invention generally pertains to devices for introducing matter into a body cavity. More specifically, the present invention pertains to delivery catheters which can be guided through body passageways to deposit living matter or medication at a desired location in the passageway. The present invention is particularly, but not exclusively, useful for depositing fertilized eggs or gametes in the fallopian tubes of a female mammal to initiate gestation.

BACKGROUND OF THE INVENTION

It is well-known that infertility is a subject which has been of great interest and concern within the medical community. This is so, in part, because it is known that infertility may result for several reasons. For example, the male and female gametes may have different antibodies which prevent fertilization. Further, it may happen that the male has a low sperm count or that the female gamete is not capable of being fertilized. There may also be mechanical factors involved. For instance, if the fallopian tubes of the female have been impaired by a disorder or have been somehow blocked, such as by a tubal ligation, it will be necessary to deposit a fertilized egg directly into the uterus, rather than the fallopian tube, before there can be any possibility of gestation.

Numerous procedures have been suggested to accomplish the intrafallopian transfer of zygotes or gametes. One of the more widely used and well-known medical procedures is laparoscopy. For laparoscopy, the fertilized egg is implanted in the distal third portion of the fallopian tube via a surgical procedure which requires an incision in the abdominal wall of the female. A syringe-like device is then inserted through the incision to deposit a fertilized egg at the desired site within the fallopian tube. Laparoscopy, however, is a surgical operation with potential complications. For example, if the required surgical incision is not properly closed, the healing process may be unnecessarily prolonged. Moreover, as with any surgical procedure requiring operative incisions, a mandatory recuperation period in the hospital is required. Also, as with other surgical procedures requiring operative incisions, there is relatively a greater risk of infection than with medical procedures that do not require operative incisions.

It is known, however, that access into body passageways need not necessarily require surgical operative incisions and, instead, may be accomplished using catheters. Indeed, catheter technology has developed markedly in several areas of medical technology. Specifically, catheters are frequently used in cardiology. As an example, for transluminal coronary angioplasty, catheters are inserted into the cardiovascular system in order to remodel a blockage or obstruction in the artery. Indeed, such a catheter is disclosed and claimed in U.S. Pat. No. 4,571,240 to Samson et al. for an invention entitled "Catheter Having Encapsulated Tip Marker". In accordance with the Samson et al. disclosure, a catheter is inserted into the coronary artery over a prepositioned guide wire until an inflatable balloon is positioned across the lesion to be compromised. In another application, U.S. Pat. No. 3,968,800, which issued to Vilasi for an invention entitled "Device for Insertion into a Body Opening" discloses a catheter-like device which is an essentially hollow tube which is useful as endotracheal tubes, bronchoscopes, vascular and cervical dilators and the like. Although these and other devices are exemplary of catheters and their varied uses, none of these devices are intended to deal with the problems associated with infertility. Further, they do not suggest the use of a catheter for depositing living matter into a body passageway for subsequent gestation. Importantly, the present invention recognizes a catheter can be used for delivering zygotes into the fallopian tubes of a female mammal without requiring operative incisions.

In light of the above, it is an object of the present invention to provide a catheter for introducing living matter into a body passageway. Another object of the present invention is to provide a delivery catheter that can accomplish intrafallopian transfer of zygotes on an outpatient basis. Still another object of the present invention is to provide a catheter which can accomplish intrafallopian transfer of zygotes through direct access of the catheter to the fallopian tube through a body orifice. Yet another object of the present invention is to provide a delivery catheter that is relatively easy to operate, relatively simple to manufacture and comparatively cost-effective for its intended purposes.

SUMMARY OF THE INVENTION

A delivery catheter is provided to initiate gestation by introducing living matter, such as zygotes or gametes, into the fallopian tubes of a female mammal. In accordance with the present invention, such a delivery catheter comprises a hollow, flexible elongated guide tube which is formed with a lumen. A tubular-shaped collection chamber having a wall is disposed as a sheath in a surrounding relationship to the guide tube. In this surrounding relationship, the distal and proximal ends of the collection chamber are joined in respective fluid-tight seals with the distal and proximal ends of the guide tube. An ejection port is formed in the wall of the collection chamber adjacent to its distal end and an actuator port is formed in the wall of the collection chamber at its proximal end. The actuator port is engageable with a syringe or other fluid-injecting device to introduce fluid into the collection chamber.

In operation, a guide wire is initially positioned through a body orifice and into the desired body passageway; for example, through the vagina and cervix, and into the fallopian tube. Before insertion of the delivery catheter into the body passageway, the delivery catheter is primed by filling the collection chamber with fluid. Zygotes are then collected in the collection chamber and held therein near the ejection port. For insertion of the delivery catheter into the body passageway, the prepositioned guide wire is slidably received into the lumen of the guide tube and the guide tube and its associated collection chamber are then advanced along the guide wire. Once the ejection port of the collection chamber is positioned at the desired site in the body passageway, ejection of the living matter (i.e. the zygotes), or medication, from the collection chamber is accomplished by introducing fluid into the collection chamber through the actuator port.

In an alternate embodiment of the present invention, the guide tube is eliminated and, instead, a guide lumen is formed into the sidewall of the collection chamber. Specifically, for this embodiment of the present invention, the collection chamber is still configured as a tubular-shaped member. The distal end of the collection chamber, however, is now either left open to form the ejection port, or is closed if the chamber. Further, a guide lumen is formed into a sidewall of the collection chamber with one opening of the guide lumen located at the distal end of the collection chamber and the other opening of the guide lumen located on the sidewall of the collection chamber. The guide lumen is dimensioned to receive the guide wire and, in the operation of this embodiment, the guide lumen is surroundingly engaged over the guide wire to advance the collection chamber along a prepositioned guide wire.

Another alternate embodiment of a delivery catheter in accordance with the present invention comprises a hollow, flexible tubular-shaped collection chamber for holding the matter to be introduced. The distal end and the proximal end of this collection chamber are closed. For this embodiment of the delivery catheter, as with the preferred embodiment, an ejection port is formed at the distal end of the collection chamber and an actuator port, which is engageable with a syringe or other fluid injecting device, is formed at the proximal end of the collection chamber. A guide catheter having a lumen for receiving the collection chamber is concentrically positionable around the collection chamber.

In the operation of this embodiment, the guide catheter is initially positioned through the vagina and into the fallopian tube. The zygote-filled collection chamber is then slidably received into the lumen of the guide catheter and the collection chamber is advanced along the guide catheter. Once the ejection port of the collection chamber is positioned at the desired site within the fallopian tube, ejection of the living matter is accomplished by introducing fluid into the collection chamber through the actuator port.

The novel feature of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a schematic showing the present invention operatively positioned through a body passageway;

FIG. 2 is a perspective view of the preferred embodiment of the delivery catheter according to the present invention;

FIG. 3 is a cross-sectional view of the catheter as seen along the line 3—3 in FIG. 2;

FIG. 4 is a cross-sectional view of the catheter as seen along the line 4—4 in FIG. 2;

FIG. 5 is a perspective view of an alternate embodiment of the delivery catheter according to the present invention;

FIG. 6 is a cross-sectional view of a portion of the catheter as seen along the line 6—6 in FIG. 5;

FIG. 7 is a cross-sectional view of a portion of the catheter shown in FIG. 5 with a flexible guide member;

DESCRIPTION OF THE PREFERRED EMBODIMENTS

Figure 8:
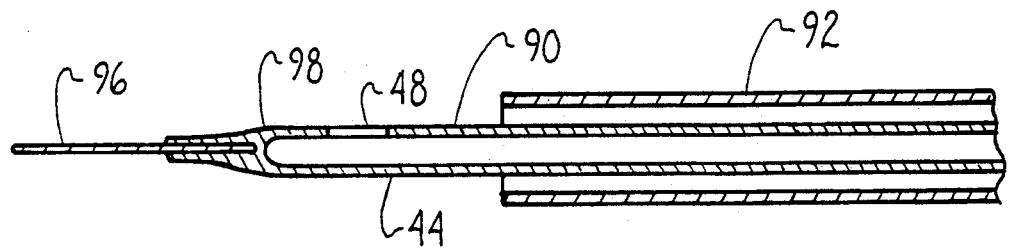
FIG. 8 is a cross-sectional view of a portion of an alternate embodiment of the catheter shown in FIG. 7 with a flexible guide member extending from the distal end of the delivery catheter.

Referring initially to FIG. 1, a delivery catheter according to the present invention is generally designated 10 and is shown operatively positioned in a female reproductive system 12.

The portions of the female reproductive system 12 shown in FIG. 1 include the ovaries 14 in which ova 16 are produced, the fallopian tubes 18 in which fertilization is normally accomplished, and the cervix 28 through which sperm must pass en route to their destiny with the ova in the fallopian tube 18. Under normal conditions of fertilization, ova 16 are conveyed from the ovary 14 to the distal third portion 20 of fallopian tube 18 by ciliated motion via the fimbria 22 and fimbria ovarica 24.

As shown in FIG. 1, delivery catheter 10 is positioned through the os externium 26 of cervix 28 through the uterus 30 and through the os 32 into the fallopian tube 18. When properly positioned, the distal end 34 of delivery catheter 10 is located in the distal third portion 20 of fallopian tube 18. FIG. 1 also shows a syringe 36 engaged with actuator port 38.

Referring now to FIG. 2, it will be seen that the delivery catheter 10 comprises an elongated, flexible guide tube 40 which is formed with a lumen 42. As shown, guide tube 40 is concentrically positioned inside a tubular-shaped collection chamber 44 which is disposed as a sheath 46 in a surrounding relationship to guide tube 40. Further, it can be seen in FIG. 2 that collection chamber 44 is formed with an ejection port 48 near its distal end 50 and with an actuator port 38 near its proximal end 52. As perhaps better appreciated with reference to FIG. 3, the proximal end 52 and distal end 50 of the collection chamber 44 are joined in respective fluid-tight seals 54 with the proximal end 58 and distal end 56 of guide tube 40. For purposes of the present invention, the fluid-tight seals 54, are made in any manner well-known in the pertinent art such as by gluing or solvent bonding.

As will be seen in cross-reference between FIGS. 2 and 3, the ejection port 48 is formed in the wall 60 of collection chamber 44 adjacent to its distal end 50. Preferably, ejection port 48 is sufficiently large enough to allow living matter to be safely ejected from delivery catheter 10. Preferably, ejection port 48 is circular and has a diameter 59 of approximately one half millimeter (0.5 mm). The actuator port 38 is also formed in the wall 60 of collection chamber 44 and although shown in FIGS. 2 and 3 as being located adjacent or near the proximal end 52 of the collection chamber 44, the actuator port 38 can be formed anywhere along wall 60 of collection chamber 44 in accordance with the desires of the operator. In any event, actuator port 38 has a fitting 64 which extends from the wall 60 of collection chamber 44 for engagement with a syringe 36 or other fluid-injecting device.

FIGS. 2, 3 and 4 also show that guide wire 66 is slidably received through the lumen 42 of guide tube 40. For purposes of the present invention, guide wire 66 may be any steerable or positionable guide wire that is well-known in the pertinent art. Importantly, guide wire 66 must be capable of being properly positioned in the body passageway and is biologically compatible with the body.

In an alternate embodiment of the present invention, as shown in FIG. 5, a delivery catheter, generally designated 68, comprises a hollow, flexible tubular-shaped collection chamber 70 which can be inserted through the lumen 74 of a guide catheter 72. More specifically, and as perhaps best seen in FIG. 6, the distal end 76 of collection chamber 70 is closed and has an ejection port 78 formed in wall 80 of collection chamber adjacent to this distal end 76. For this embodiment, an actuator port 82, shown in FIG. 5, is formed in wall 80 at the proximal end 84 of collection chamber 70 which is engageable with a syringe 36 or other fluid-injecting device for purposes to be subsequently discussed in conjunction with the operation of the present invention. As can be appreciated by reference to FIG. 6, delivery catheter 68 is insertable through the lumen 74 of a guide catheter 72. Moreover, like guide wire 66, guide catheter 72 is steerable or positionable into a body passageway.

As seen in FIG. 7, a delivery catheter, generally designated 86, can include a flexible steering member 88 which is embedded within the wall 90 of collection chamber 70. More specifically, steering member 88 can be used and manipulated in a manner similar to that of guide wire 66. Thus, with a member 88 incorporated as part of collection chamber 70, the collection chamber 70 can, itself, be positioned in the body passageway without using the positioning capability of either a guide wire 66 or a guide catheter 72.

FIG. 8 shows an alternate embodiment for the delivery catheter of the present invention in which a guide element 96 extends from the distal end 98 of a collection chamber 44. The actual attachment of the guide element 96 to distal end 98 can be accomplished by any means well-known in the pertinent art, such as by solvent bonding or heat bonding. As intended for this embodiment of the present invention, guide element 96 can be prebent and used in a manner well-known in the pertinent art to place the collection chamber 44 of delivery catheter 10 through the intended body passageway. As will be appreciated by the skilled artisan, the guide catheter 92 can by used to assist in the proper positioning of the collection chamber 44. Importantly, if the guide catheter 92 extends over ejection port 48 formed into the wall 90 of collection chamber 44, guide catheter 92 must be withdrawn in a proximal direction to expose the ejection port 48 before any living matter or medications can be dispensed from collection chamber 44 through ejection port 48.

Figure 9:
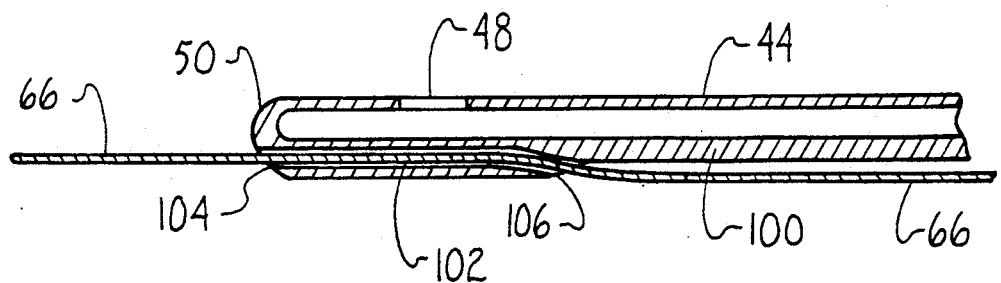
FIG. 9 is a cross-sectional view of a portion of another alternate embodiment of the present invention as would be seen along the line 3—3 in FIG. 2.

In FIG. 9, another embodiment of the present invention is shown in which the side wall 100 of collection chamber 44 is formed with a guide lumen 102. Specifically, guide lumen 102 has an opening 104 which is positioned at the distal end 50 of collection chamber 44. Also, guide lumen 102 has another opening 106 which is located proximally along the sidewall 100 from opening 104 to form a passageway through which guide wire 66 can pass. With this configuration, the guide wire 66 can be prepositioned in the particular body passageway where collection chamber 44 is to be inserted and the collection chamber 44 can receive the guide wire 66 through the guide lumen 102. Collection chamber 44 is then advanceable over guide wire 44 to position ejection port 48 of collection chamber 44 at the desired location in the body passageway.

OPERATION

In its operation, the delivery catheter 10 of the preferred embodiment is first primed with a biologically compatible fluid, such as a saline solution, and a syringe 36 is operatively engaged to the actuator port 38 of collection chamber 44. The ejection port 48 of collection chamber 44 is then placed in a container (not shown) which holds the zygotes 94 that are to be introduced into the fallopian tube 18, and the zygotes 94 are drawn into collection chamber 44 through ejection port 48 by proper operation of the syringe 36. It will be appreciated that delivery catheter 10 can also be primed with gametes instead of zygotes.

The guide wire 66 is initially inserted through a body orifice, such as the vagina of a female mammal, and is disposed with its distal end 76 positioned in the distal third portion 20 of fallopian tube 18. The guide tube 40 of delivery catheter 10 is engaged with the guide wire 66 to slidably receive guide wire 66 into the lumen 42 of the guide tube 40, and delivery catheter 10 is then advanced into position along guide wire 66. With the ejection port 48 of collection chamber 44 positioned in the distal third portion 20 of fallopian tube 18, ejection of zygotes 94 from collection chamber 44 is accomplished by introducing fluid into the collection chamber 44 through the actuator port 38. In accordance with the present invention, this introduction of fluid is accomplished by use of a syringe 36 or other fluid-injecting device.

In the operation of the alternate embodiment of the present invention, a guide catheter 72, rather than a guide wire 66, is used. For this embodiment, the priming of collection chamber 70, and the collection of zygotes 94 into collection chamber 70 is accomplished essentially as disclosed above for the preferred embodiment. Then, once guide catheter 72 is prepositioned into the body passageway, the collection chamber 70 is inserted through the lumen 74 of guide catheter 72 and advanced along guide catheter 72 until the distal end of the guide catheter 72 is positioned through the vagina and into the distal third portion 20 of fallopian tube 18. Once the ejection port 78 is positioned at the distal third portion 20 of fallopian tube 18, ejection of zygotes 94 is accomplished by introducing fluid into the collection chamber 70 through the actuator port 38 by a syringe 36 or other fluid-injecting device.

While the particular delivery catheter as herein shown and disclosed in detail is fully capable of obtaining the objects and providing he advantages herein before stated, it is to be understood that it is merely illustrative of the presently preferred embodiments of the invention and that no limitations are intended to the details of construction or design herein shown other than as described in the appended claims.

I claim:

1. A method for depositing biological matter in a fallopian tube of a female mammal which comprises the steps of:
   providing a delivery catheter having a collection chamber with an ejection port and an actuator port;
   placing said biological matter in said collection chamber;
   inserting a portion of said collection chamber including said ejection port through a body orifice into said fallopian tube;
   introducing a displacement fluid into said collection chamber via said actuator port;
   displacing said biological matter from said collection chamber with said displacement fluid into said fallopian tube via said ejection port; and
   withdrawing said delivery catheter from said body orifice.

2. A method as recited in claim 1 wherein said portion of said collection chamber is steered into said fallopian tube with a guide means operatively engageable with said collection chamber.

3. A method as recited in claim 2 wherein said guide means comprises a guide wire, prepositionable through said orifice and into said fallopian tube; and a tube associated with said collection chamber, said tube having a lumen for slidably receiving said guide wire therethrough to advance said chamber along said guide wire.

4. A method as recited in claim 2 wherein said collection chamber comprises a hollow tube having an open end and a closed end, said ejection port being positioned adjacent said closed end of said tube and said open end of said tube defining said actuator port; and said guide means comprises a flexible member extending lengthwise from said collection chamber for positioning said collection chamber in said fallopian tube.

5. A method as recited in claim 1 further comprising introducing a transport fluid into said collection chamber before introducing said displacement fluid into said collection chamber.

6. A method as recited in claim 1 further comprising introducing a transport fluid into said collection chamber before placing said biological matter in said collection chamber.

7. A method as recited in claim 5 wherein sad transport fluid and said displacement fluid have substantially the same composition.

8. A method as recited in claim 1 wherein said transport fluid is displaced into said fallopian tube with said biological matter.

9. A method as recited in claim 1 wherein said body orifice is a vagina.

10. A method as recited in claim 1 wherein said biological matter is a zygote or a gamete.

11. A method as recited in claim 1 wherein said displacement fluid is introduced into said collection chamber from a syringe in fluid communication with said actuator port.

12. A method as recited in claim 1 wherein said biological matter is placed in said collection chamber proximal said ejection port.

13. A method as recited in claim 1 wherein said biological matter is placed in said collection chamber via said ejection port.

14. A method as recited in claim 6 wherein said biological matter is placed in said collection chamber via said ejection port by withdrawing a portion of said transport fluid from said collection chamber via said actuator port with a syringe while said biological matter is maintained in fluid communication with said ejection port, thereby drawing said biological matter into said collection chamber through said ejection port.

15. A method as recited in claim 11 wherein said syringe operatively engages said actuator port.

16. A method for depositing biological matter in a fallopian tube of a female mammal which comprises the steps of:
providing a delivery catheter having a collection chamber with an ejection port and an actuator port;
introducing a transport fluid into said collection chamber;
placing said biological matter in said collection chamber proximal said ejection port by withdrawing a portion of said transport fluid from said collection chamber via said actuator port with a syringe in operative engagement with said actuator port while said biological matter is maintained in fluid communication with said ejection port, thereby drawing said biological matter into said collection chamber through said ejection port;
inserting a portion of said collection chamber including said ejection port through a body orifice into said fallopian tube;
introducing a displacement fluid with said syringe into said collection chamber via said actuator port;
displacing said biological matter from said collection chamber with said displacement fluid into said fallopian tube via said ejection port; and
withdrawing said delivery catheter from said body orifice.

* * * * *